Figure 3:
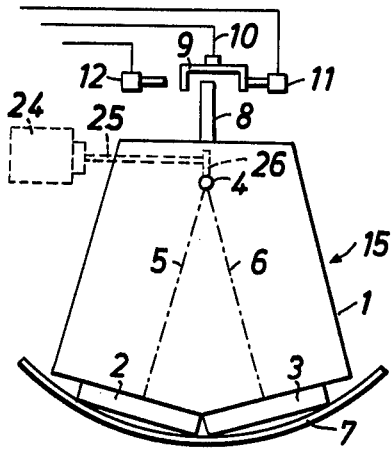

United States Patent [19]
Kretz

[11] 4,281,549
[45] Aug. 4, 1981

[54] EQUIPMENT FOR DISPLAYING SECTION IMAGES OF OBJECTS SUBJECTED TO ULTRASONIC EXAMINATION

[75] Inventor: Carl Kretz, Zipf, Austria

[73] Assignee: Kretztechnik Gesellschaft m.b.H., Zipf, Austria

[21] Appl. No.: 63,241

[22] Filed: Aug. 3, 1979

[30] Foreign Application Priority Data

Jan. 11, 1979 [AT] Austria ................................. 199/79

[51] Int. Cl.³ ............................................ G01N 29/04
[52] U.S. Cl. ......................................... 73/626; 73/633
[58] Field of Search .......................... 73/626, 633, 641; 128/660

[56] References Cited

U.S. PATENT DOCUMENTS

| | | | |
|---|---|---|---|
| 3,439,530 | 4/1969 | Flaherty et al. ...................... | 128/660 |
| 3,955,561 | 5/1976 | Eggleton ............................... | 128/660 |
| 4,010,634 | 3/1977 | Baumgartner ......................... | 73/620 |
| 4,102,204 | 7/1978 | Kretz ..................................... | 73/641 |

*Primary Examiner*—Anthony V. Ciarlante
*Attorney, Agent, or Firm*—Kurt Kelman

[57] ABSTRACT

Equipment is disclosed which serves to trace B-scan section displays of specimens and comprises a sound transducer head, which is oscillated by a scanning mechanism and projects sound beams, which scan the section to be displayed. The echoes which originate in response to these sound beams are displayed on a fluorescent screen at locations which are associated with the locations at which said echoes have originated. The sound transducer head comprises two sound transducers, the axes of which in the plane in which they are oscillated include an angle which is not in excess of the angular range of oscillation. As a result, the pitch with which the section to be displayed is scanned by ultrasonic beams is decreased and/or the angular velocity of the sound transducer head may be decreased.

11 Claims, 7 Drawing Figures

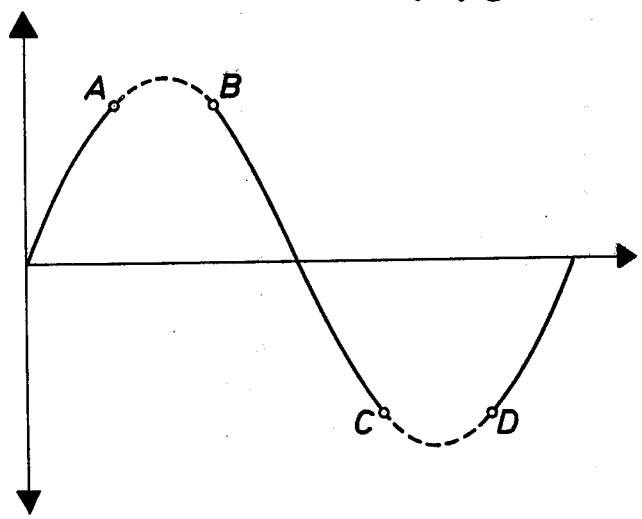
FIG.1
FIG.2
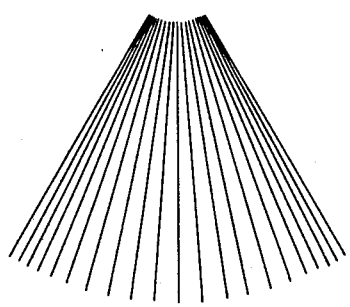

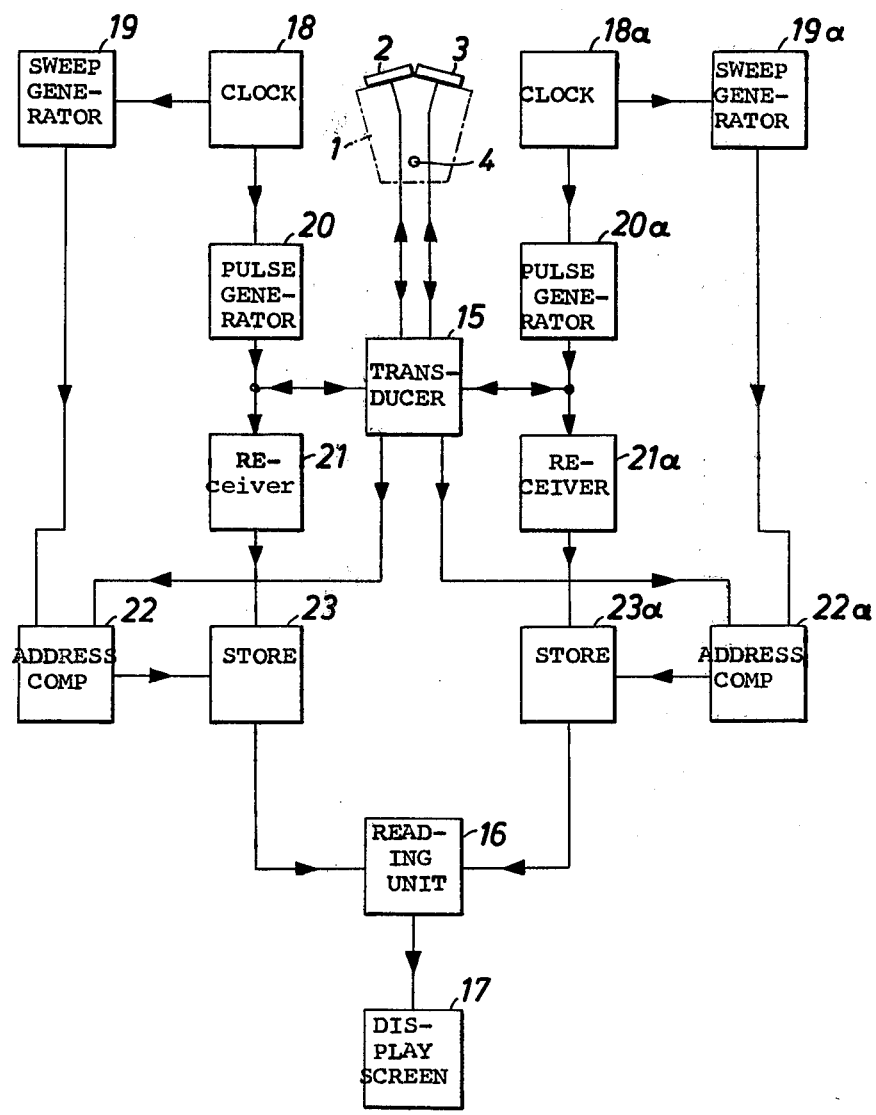

EQUIPMENT FOR DISPLAYING SECTION IMAGES OF OBJECTS SUBJECTED TO ULTRASONIC EXAMINATION

This invention relates to equipment for displaying section images of objects subjected to ultrasonic examination, comprising sound transducer means and a scanning mechanism for oscillating said sound transducer means so that when the sound transducer means are applied to a specimen a section of the latter is scanned in a generally triangular or trapezoidal area by sound beams projected by the sound transducer means, whereafter echoes originated in said specimen are applied to or in response to said beams are received and can be displayed on a fluorescent screen at locations which are geometrically coordinated with the locations at which said echoes have originated.

Equipment of that kind may be used, inter alia, for medical examinations. In a preferred application, it permits of a tracing of moving section displays. To that end, the section plane to be displayed or part of said plane is completely scanned several times per second so that motions performed inside the human body, e.g., the movements of the valves of the heart, can be displayed on the fluorescent screen. A so-called parallel scan may be employed, in which the sound beam is displaced parallel to itself although in that case the use of a mechanically moved sound transducer head involves the problem that it is difficult to ensure an adequate coupling of the sound throughout the length of the path of the sound transducer head. Equipment of the kind mentioned first may be used for the same purpose and affords the advantage that the edges of the sector which is displayed diverge from the point of application of the sound transducer to the specimen so that a relatively small window is sufficient for introducing the sound and owing to the divergent edges of the display the human body can be examined in a region which widens from the window. A basically triangular section display will be obtained if the pivotal axis of the sound transducer head is disposed on the surface of the body being examined. If the pivotal axis is parallel to and outwardly spaced from the surface of the body, a trapezoidal section display will be obtained. Because the window is small, sound can be introduced even between the ribs.

In equipment of this kind, the scanning mechanism can either oscillate the entire sound transducer head although this can be accomplished only if the sound transducer head is pivotally movable about its point of application to the specimen, or the scanning mechanism may be operable to oscillate the sound transducer itself and the housing of the sound transducer head is provided with a suitable guide for the sound transducer. It will be understood that the sound transducer is provided with a damping member, electrical connections etc.

When the sound transducer head or sound transducer is driven to oscillate, the oscillating motion is derived in most cases from a constant rotation of a motor so that the angular position is an approximately or exactly sinusoidal function of time and the angular velocity is not constant. If such equipment is operated as usual at a constant pulse repetition rate, that varying angular velocity will result in a non-uniform scanning of the section plane that is to be displayed. This results in the severe disadvantage that the regions corresponding to the marginal portions of the display are scanned with a small pitch, although these regions are in most cases of minor interest, and the regions corresponding to the central portion of the display are scanned with a large pitch although they are usually most interesting. As the angular velocity of the oscillating sound transducer head or sound transducer is highest in the region corresponding to the central portion of the display and a higher angular velocity involves a lower useful penetration of the sound beam because there is an apparent loss of sensitivity of the sound transducer head or sound transducer if sound waves are incident thereon which are not aligned with nor parallel to the axis of the sound transducer but travel at an angle to that axis. This effect will be particularly pronounced with sound transducer heads or sound transducers which have the high directivity that is required for section displays. The larger the distance from a reflecting surface to the sound transducer, the longer will be the time taken by a sound wave produced by a projected pulse to reach that reflecting surface and by the echo to return to the sound transducer. These disadvantages have been at least partly eliminated by various known designs. In a known arrangement, only that part of the movement of the sound transducer head is utilized for the display in which the scanning speed does not change at an excessively high rate but is approximately constant. As a result, the marginal portions of the display are cut off and the sound transducer head operates only in the region in which it moves at high speed. For this reason that proposal is not satifactory. It involves the additional problem that an improved diagnosis often requires not only an examination of the section display but an additional, separate evaluation of at least part of the signals obtained during the examination, such as echoes from a region corresponding to a specific portion of the display, particularly its central region, by a so-called A-scan, or, in examinations of the heart, a time-motion display of the so-called ultrasonic cardiogram. For that purpose, signals derived from a specific region that is scanned may be extracted but this will create in the display a hole, which will be the larger and the more disturbing the larger is the scanning pitch. U.S. Pat. No. 4,010,634 discloses a method in which the motion of the sound transducer is stopped at the point at which a time-motion display is desired. This stopping will be increasingly difficult if the sound transducer was moved at a high velocity, as is the case in the region corresponding to the central portion of the display when the known drive system is employed. In most cases, the time-motion display is desired for a point in that central portion.

In an endeavor to make possible a scanning with a pitch which is as uniform as possible, it has been proposed in Opened German Specification No. 2,448,595 not to derive the motion of the sound transducer from a rotary motion, such as the motion of a crank, but to couple the sound transducer to the axis of a galvanometer, which is controlled by a voltage generator which generates a triangular waveform so that the sound transducer is theoretically oscillated at constant angular velocity. The practice of that proposal involves forces of inertia, which are particularly strong at the points of reversal so that the motion is not uniform.

U.S. Pat. No. 4,102,204 discloses equipment which is of a different kind and comprises a wheel, which rotates at uniform speed and at its periphery carries a plurality of sound transducers, which are activated whenever they move past a window through which the sound is transmitted. In that arrangement, a constant angular velocity is maintained and the sound transducer can be directly coupled to the specimen to be examined, as is important for a high depth of penetration and a sufficiently high pulse repetition rate. But in such an arrangement it is also difficult to suddenly stop the wheel in predetermined positions, and the arrangement is expensive. Besides, it requires a large number of transducers which must be exactly matched in a complicated operation.

In equipment of the kind described first hereinbefore, the invention resides essentially in that the sound transducer means comprise two sound transducers, each of which consists of a transmitter and receiver and which are inclined toward each other in the plane of oscillation and the axes of which include an angle which is not in excess of the angular range of oscillation, and the echoes received by both sound transducers are displayed on the fluorescent screen.

As a result, the field angle of the display exceeds the angular range of oscillation and will be almost twice that angular range if the angle included by the axes of the sound transducers is slightly smaller than said angular range.

Where the sound transducer head according to the invention is used, each sound transducer scans only an associated region of the plane which is to be displayed so that lower angular velocities will be sufficient to cover a given area than in the known apparatus. When the motion is reversed, the transducer which is scanning the region corresponding to the central portion of the display will always be active. If the angular velocity varies according to a sine function, the region corresponding to the central portion of the display will be scanned at a lower velocity, i.e., with a smaller pitch, so that the highest sensitivity and the highest depth of penetration will be obtained in that region. The small scanning pitch ensures that there will be virtually no disturbing holes when signals are extracted for a different mode of display. Because the region corresponding to the central portion of the display is scanned at low or zero velocity, the transducers can be stopped without difficulty for the extraction of signals for the other mode of display.

The equipment according to the invention can be embodied in various forms. The least structural expenditure will be involved if the two sound transducers of the sound transducer head can be connected in alternation to a common ultrasonic control and display unit. In that case, the connections from the two sound transducers to the ultrasonic control and display unit may be changed over at a frequency which is twice the frequency of oscillation of the sound transducer head and the change-over switch may be operated whenever the motion of the sound transducer head is reversed.

According to a preferred feature, the angle included by the axes of the sound transducers is smaller than the angular range of oscillation so that the sound beams generated by the two sound transducers and the portions scanned by them overlap in the central portion of the display, and the change-over switch is operated during the overlap period.

According to a modification, the connections between the sound transducers and the ultrasonic control and display unit are arranged to be changed over at a frequency which is a multiple of the frequency of oscillation so that the two sound transducers are used in alternation to generate the section display in both halves thereof.

In a more expensive embodiment, each sound transducer has separate pulse-generating and signal-processing means associated with it and a common fluorescent screen is associated with both sound transducers. This arrangement affords the advantage that both sound transducers can operate virtually at the same time. This operation can be made possible in various ways. In one arrangement, the fluorescent screen is a component of a two-beam cathode ray tube, the beams of which are controlled by respective receivers, which are associated with respective sound transducers.

According to another modification, each receiver has associated with it a store for storing the signals at addresses associated with the locations at which the corresponding echoes have originated, and the display on the fluorescent screen is controlled by a common reading unit, which is associated with both stores and reads the contents of the stores independently of the order in which the signals have been received by the stores. The stores may consist of any addressable stores, inclusive of picture storage tubes. Alternatively, each store may be preceded by an address computer and in that case the reading unit may read the signals from both stores in rapid alternation so that both halves of the display will be traced on the fluorescent screen virtually at the same time.

A change-over switch may be provided, which is adapted to extract signals, particularly whenever the motion is reversed, so that said signals can be displayed in a different mode (A-scan, TM-scan) on the same or a separate fluorescent screen.

Figure 4:
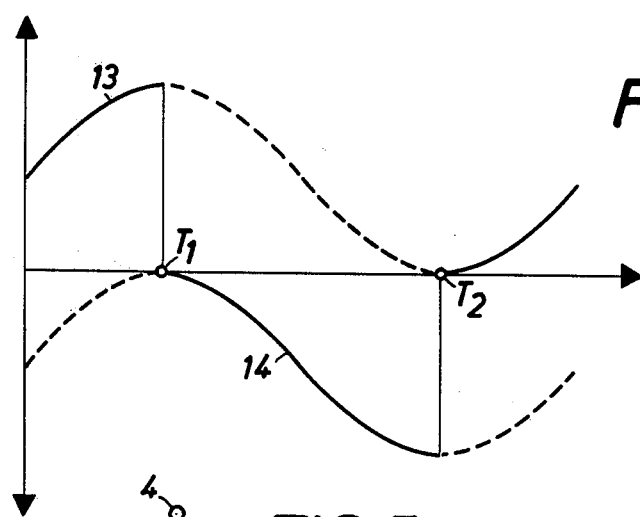
Figure 5:
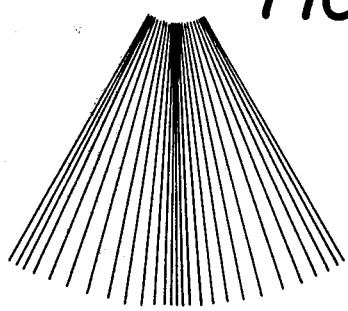
Figure 5A:
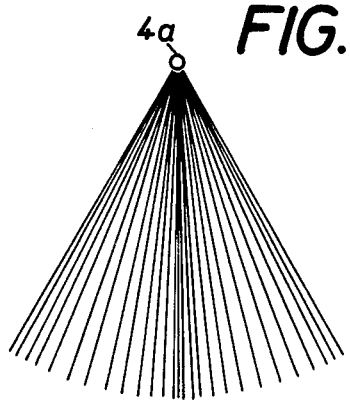

The invention is illustrated by way of example on the accompanying drawings, in which FIGS. 1 and 2 show a motion diagram and a scanning raster diagram for an illustration of the prior art, FIG. 3 is a diagrammatic elevation showing a sound transducer head, FIGS. 4, 5, and 5a are views corresponding to those of FIGS. 1 and 2 and show an arrangement according to the invention and FIG. 6 is a block circuit diagram showing a portion of equipment according to the invention.

In FIG. 1, the angular velocity of an oscillating sound transducer of a conventional sound transducer head is plotted against time. The sound transducer is oscillated within an angle of ±30°, i.e., a total angle of 60°. It is apparent that the angular velocity varies according to a sine curve. It is also apparent from FIG. 1 that when only the linear or approximately linear portions of the velocity curve are used, i.e., the curve is cut off between points AB and CD, the motion will be more uniform but the slower portions of the motion will be eliminated.

The resulting scanning raster is shown with great exaggeration in FIG. 2. It is apparent that the pitch is much higher in the marginal portions of the scanned sector than in the regions corresponding to central portions of the display.

FIG. 3 shows a sound transducer head according to the invention. The sound transducer head comprises a holder 1, which constitutes the required damping member and in which two sound transducers 2, 3 are mounted, which are inclined to each other at a certain angle. The two sound transducers 2, 3 are adapted to be oscillated about an axis 4, which is disposed outside of and spaced from the specimen to be examined. The sound transducers are oscillated by a scanning mechanism, which is indicated only by dotted lines and comprises a motor 24, which drives the sound transducers 2, 3 by means of a connecting rod 25 and a crank 26. The axis 4 is at the point of intersection of the geometrical axes 5, 6 of the sound transducers. The sound transducer head is closed in front by a curved protective layer, which has a center of curvature on the axis 4. The sound transducers 2, 3 are coupled to the protective layer 7 by a suitable liquid, which has been filled into the housing of the sound transducer head. That housing is not shown. The angle included by the axes 5, 6 of the sound transducers 2, 3 is not in excess of the predetermined angular range of oscillation and is preferably somewhat smaller.

As a result, the field angle of the display exceeds the angular range of oscillation and will be almost twice that angular range if the angle included by the axes of the sound transducers is slightly smaller than said angular range.

In one embodiment, the connections from the two sound transducers and an ultrasonic control and display unit are changed over at a frequency which is a multiple of the frequency of oscillation.

In the embodiment shown on the drawing, the change over is so controlled that the two sound transducers are connected to the ultrasonic control and display unit during respective half-periods of the oscillation of the sound transducer head and the change over is effected whenever the motion is reversed. This can be accomplished in the embodiment shown in that the holder 1 carries a coupling element 8, which extends into and can engage a contact bridge 9 so that in the final phase of each stroke of the coupling member 8 the latter carries the contact bridge 9 along so as to disengage it from one contact 11 and engage it with another contact 12 and vice versa. The contact bridge is connected to a lead 10.

The motions performed to trace a display are shown in FIG. 4. It is again assumed that the field angle of the section display should be 60°. The curve 13 is proportional to that of FIG. 1 and shows the angular range covered by the sound transducer 3. The curve 14 shows the angular range covered by the sound transducer 2. The solid portion of each curve indicates the region in which the sound transducer is active. Starting in the central position, the sound transducer 3 is initially connected and traces the right-hand portion of the display (FIG. 5) between the angles +15° and +30°. At the time $T_1$ when the motion is reversed, a change over is effected to the sound transducer 2, which now traces the left-hand portion of the display, beginning at the center, between the angles 0° and −30°. At the time $T_2$ when the motion is reversed once more, the sound transducer 3 is connected, which now traces the remaining portion of the display between the angles 0° and +15°. Because these tracing cycles are repeated several times a second and the fluorescent screen has a certain persistence, the viewer will always see the entire section display, also because his eyes have a certain inertia. As is apparent from FIG. 5a, the axis of oscillation 4a may alternatively be disposed near the surface of the sound transducer head and the region where it contacts the specimen to be examined. In that case, an approximately triangular area of the section will be scanned.

It will be sufficient for each sound transducer to cover approximately one-half of the angular range of oscillation so that the accelerating forces are smaller although the total weight is higher than where only one sound transducer is employed. The smallest scanning pitch will be obtained in the regions in which the motion is reversed. If the angle included by the axes of the sound transducers is smaller than the angular range of oscillation, the displays traced by the two sound transducers will overlap. During the tracing of the central portion of the display, signals for a different display mode (ultrasonic cardiogram or A-scan) can be extracted. Owing to the overlap, no holes will be apparent in the display and even the extraction of a single line in non-overlapping portions of the display will not be disturbing because the line pitch is high in the central portion.

If the change over frequency is twice the frequency of oscillation and the change over is effected whenever the motion is reversed, the sound beam will always turn in the same direction during the tracing of both halves of the display. As a result, there will be no distortion caused by a backlash in the drive means.

With reference to FIG. 6, an embodiment will now be described in which the scanning pitch may be one-half the scanning pitch obtained in the preceding embodiment or the scanning frequency may be doubled for the same scanning pitch. This requires that the beams emitted by the two sound transducers 2, 3 are so divergent that these sound beams and the echoes resulting therefrom will not interfere, and that a cross-talk between the sound transducers is prevented. The beams will always be sufficiently divergent if a conventional field angle is selected.

Only those elements have been shown in FIG. 6 which are required in addition to or differ from the conventional elements of a standard section display apparatus.

The two transducer heads 2, 3 shown in FIG. 6 are associated with different units, which are provided for each sound transducer. Common to both sound transducers 2, 3 are only a common sound transducer head 1, its circuitry 15 and drive means, a common reading unit 16, and a common display unit 17, such as a fluorescent screen.

Each unit comprises a clock 18 or 18a, which triggers a sweep generator 19, 19a and a pulse generator 20, 20a. The generated pulses are fed to the respective sound transducers 2 and 3 of the sound transducer head 1 via its circuitry 15. The two clocks 18, 18a need not be synchronized.

A separate receiver 21 or 21a is associated with each of the sound transducers 2 and 3. The term "receiver" covers not only an amplifier for the signals which are derived in the sound transducers 2, 3 from the echoes, but all other means for processing or shaping of the signals, such as threshold controls, filters, depth compensators etc.

Position-indicating signals are transmitted to address computers 22, 22a from the transducer head circuitry 15 or from the scanning mechanism which may be accommodated in the transducer head 1 and drive the sound transducers 2, 3 or which may drive the entire sound transducer head 1. The computers 22, 22a process the positioning signals as well as the sweep voltages applied from sweep generators 19, 19a to compute the addresses with which each incoming echo signal is associated. The address signals from the computers 22, 22a and the amplified echo signals from the amplifiers 21, 21a are received by the stores 23, 23a, in which the echo signals are now stored at addresses associated with the locations at which the corresponding echoes have originated, until all signals for tracing one-half of the display have been stored in each of the two stores 23, 23a. The two stores are then retrieved in alternation by the reading unit 16 and the retrieved signals are delivered to the display unit 17 and are displayed by the latter virtually simultaneously.

What is claimed is:

1. Equipment for the ultrasonic examination of a specimen in a section plane and for tracing moving section plane displays in response to said examination, comprising
    transducer means including two ultrasonic transducers having axes which lie in a common plane and include a predetermined angle with each other, each of said sound transducers being operable to project an ultrasonic beam, to receive echoes originated in response to said beam and to derive electric echo signals from such echoes received,
    a scanning mechanism for oscillating said transducer means in said plane through a predetermined angular range, which is at least as large as the angle included by said axes, and
    display means comprising a fluorescent screen and operable to display said echo signals on said fluorescent screen at locations associated with the locations at which said echoes have originated.

2. Equipment as set forth in claim 1, which comprises an ultrasonic control and display unit including said display means and
    a change-over switch operable to connect said two transducers in alternation to said ultrasonic control and display unit.

3. Equipment as set forth in claim 2, in which
said scanning mechanism is operable to oscillate said transducer means at a given frequency of oscillation and
said change-over switch is arranged to change over the connections from said two transducers to said ultrasonic control and display unit whenever the motion of said transducer means is reversed.

4. Equipment as set forth in claim 2, in which
the angle included by said axes is smaller than said angular range of oscillation,
said two transducers are arranged to control the tracing of respective portions of said display on said fluorescent screen, which portions overlap in a predetermined area, and
said change-over switch is arranged to change over the connections from said transducers to said ultrasonic control and display unit during the tracing of said display in said predetermined area.

5. Equipment as set forth in claim 2, in which
said scanning mechanism is operable to oscillate said transducer means at a given frequency of oscillation and
said change-over switch is arranged to change over the connections from said two transducers to said ultrasonic control and display unit at a frequency which is a multiple of said frequency of oscillation.

6. Equipment as set forth in claim 1, in which
first and second control means are operatively connected to respective ones of said sound transducers and operable to control the respective sound transducer and to process said echo signals derived by it and
said display means are operatively connected to said control means and comprise a fluorescent screen associated with both said sound transducers.

7. Equipment as set forth in claim 6, in which
said display means comprise a cathode ray tube which includes said fluorescent screen and is operable to generate first and second electron beams and
said first and second control means are arranged to control the generation of said first and second beams.

8. Equipment as set forth in claim 6, in which
each of said control means comprises an addressable store arranged to receive said echo signals from the associated transducer and to store said echo signals at addresses associated with the locations at which the corresponding echoes have originated, and
a reading unit is provided, which is operable to retrieve said echo signals from said stores independently of the sequence in which said echo signals have been received by said stores and to deliver the signals thus retrieved to said display means.

9. Equipment as set forth in claim 8, in which
each of said stores is operatively connected to an associated address computer for controlling the addresses at which said echo signals are stored and
said reading unit is operable to retrieve said signals from said stores in rapid alternation.

10. Equipment as set forth in claim 1, in which
said display means are arranged to display said echo signals in a predetermined mode and
a change-over switch is provided, which is operable to extract echo signals derived from said transducers for a display in a different mode.

11. Equipment as set forth in claim 10, in which said change-over switch is arranged to extract said echo signals whenever the motion of said transducer means is reversed.

* * * * *